(12) United States Patent  
Schoeppe (10) Patent No.: US 6,732,598 B2
(45) Date of Patent: May 11, 2004

(54) AUTOMATIC PIPETTOR WITH A SINGLE-ROW, MULTI-CHANNEL PIPETTING HEAD

(75) Inventor: Torsten Schoeppe, Jena (DE)

(73) Assignee: CyBio Instruments GmbH, Jena (DE)

( * ) Notice: Subject to any disclaimer, the term of this patent is extended or adjusted under 35 U.S.C. 154(b) by 250 days.

(21) Appl. No.: 09/848,845

(22) Filed: May 4, 2001

(65) Prior Publication Data

US 2001/0039843 A1 Nov. 15, 2001

(30) Foreign Application Priority Data

May 5, 2000 (DE) .......................... 100 22 693

(51) Int. Cl.$^7$ ................................. G01N 1/00
(52) U.S. Cl. .................................. 73/864.14
(58) Field of Search .................. 73/863.32, 864.14, 73/864.17, 864.18; 422/100

(56) References Cited

U.S. PATENT DOCUMENTS

| 4,478,094 A | 10/1984 | Salomaa et al. |
| 4,555,957 A | 12/1985 | Frankel et al. |
| 4,779,467 A * | 10/1988 | Rainin et al. ............ 73/864.17 |
| 5,061,449 A * | 10/1991 | Torti et al. ............... 73/864.14 |
| 5,413,000 A * | 5/1995 | Stark et al. .............. 73/864.23 |
| 5,599,500 A | 2/1997 | Jones |
| 5,915,284 A * | 6/1999 | Meltzer et al. .......... 73/864.17 |

FOREIGN PATENT DOCUMENTS

| DE | 31 01 696 | 8/1982 |
| DE | 197 46 455 | 5/1999 |
| EP | 0 114 686 | 8/1984 |
| WO | WO 99/26723 | 6/1999 |

* cited by examiner

*Primary Examiner*—Robert Raevis
(74) *Attorney, Agent, or Firm*—Reed Smith LLP (57) ABSTRACT

Automatic pipettor with a single-row, multi-channel pipetting head, with tip ejector mechanism by which the pipette tips attached to pipettes arranged in a row are successively removed and which, by means of the movable construction of a lifter arranged below the pipetting head and carrying, e.g., a microtitration plate, can be used in an all-purpose manner for different microtitration plates in the direction of the pipettes and the movability of the pipetting head in a direction orthogonal thereto.

4 Claims, 8 Drawing Sheets

F I G. 4

AUTOMATIC PIPETTOR WITH A SINGLE-ROW, MULTI-CHANNEL PIPETTING HEAD

BACKGROUND OF THE INVENTION a) Field of the Invention

The invention is directed to an automatic pipettor with a single-row, multi-channel pipetting head.

b) Description of the Prior Art

An arrangement of this kind is known in a very broad sense from U.S. Pat. No. 4,478,094.

The introduction of the first microtitration plates (MTPs) in laboratories of large institutes and research facilities and the development of automatic pipetting devices launched by this represented a substantial contribution to automatic processing of liquid samples and automation of the associated handling processes.

As a result of the mechanization of test processes which this entailed, it became desirable that the arrangement pattern of sample vessels to be processed automatically should always be the same. Accordingly, with the continued development of MTPs spurred on by the permanent demand for higher sample throughput and smaller sample volumes, the grid-shaped arrangement of wells (sample receptacles) in rows and columns created with the first MTPs was retained. In the meantime, besides the first 96-well MTPs with 12×8 wells, 192-well, 384-well, 864-well and 1536-well MTPs have become commercially available. Although the MTPs have many times the number of wells of their precursors, it was possible to maintain the outer dimensions by making the wells smaller, so that some of the instrument technology for MTP handling that has developed in many different ways in the interim can be used substantially independent from the respective number of wells. Accordingly, hardly any new requirements have arisen from the further development of the MTPs for the instrument technology concerned with their handling, whereas the increased number of wells and reduced size of the wells on the same area have placed high demands on the further development of automatic pipetting devices.

Not only must continually smaller sample volumes be pipetted in increasingly narrow grid dimensions, and this as quickly as possible, but there is also a demand for an all-purpose applicability of the automatic pipettor for different MTPs.

The automatic pipettors known from the prior art have met these demands in different ways.

In principle, automatic pipettors can be differentiated into automatic pipettors with single-channel pipetting heads, those with single-row, multi-channel pipetting heads and those with multi-row, multi-channel pipetting heads; automatic pipettors with a single-channel pipetting head are excluded from laboratory processes demanding a high sample throughput.

The advantage of automatic pipettors with a multi-row, multi-channel pipetting head consists in that the wells of multiple rows or all rows of the MTPs are filled simultaneously. An automatic pipettor of this kind with 96 pipette tips, trade name CyBi-Well 96, is available from CyBio AG. The pipette tips are arranged in the same grid (8×12) as the wells of a commercially available 96-well MTP. Accordingly, a 96-well MTP can be filled simultaneously by this automatic pipettor. The CyBi-WELL 96/384/1536 automatic pipettor is an expanded version which can fill a 384-well (16×24) in four positioning steps and a 1536-well MTP (32×48) in sixteen positioning steps. The positioning steps are carried out by a horizontal movement of the lifter carrying the MTP in the direction of the wells arranged in rows and columns. These automatic pipettors are fundamentally unsuited for differentiated sample processing in the wells of an MTP, e.g., for preparing different dilution series.

The automatic pipettors with a single-row, multi-channel pipetting head which only fill the wells of one row simultaneously have proven advantageous for an application of this kind.

Consequently, depending on the requirements of the user, automatic pipettors with single-row or multi-row, multi-channel pipetting are more advantageous.

A real disadvantage of the automatic pipettors with single-row, multi-channel pipetting head consists in that they have so far been designed exclusively for processing 96-well MTPs.

In principle, automatic pipettors of the type described above comprise a guide path with a carriage which is movable in horizontal direction and which has receptacle places for the MTPs or other vessels, a pipetting head which is arranged above the latter and which has pipette tips arranged in a plurality of rows orthogonal to the movement direction, and a lifter arranged below the pipetting head and movement plane of the carriage, which lifter raises and lowers an MTP or other vessels positioned above it vertically in the direction of the pipette tips.

With the CyBi-WELL 96/384/1536 automatic pipettor mentioned above, the MPT can be moved into multiple positions to the pipetting head located above it by means of an additional horizontal movement of the lifter in two directions, so that all MTPs having a number of wells equal to a multiple of 96 can be filled with only 96 tips.

The pipetting head does not execute a horizontal movement in any of the known automatic pipettors with a single-row, multi-channel pipetting head. The tip ejector mechanism requires a basic design solution for the pipetting head leading to a substantially more heavyweight construction and, therefore, to greater inertia than would be possible for pipetting heads without a tip ejector mechanism.

The design solution for the tip ejector mechanism is approached in very different ways in the pipetting heads known from the prior art. However, the solutions have the similarity that the pipette tips (generally 8 or 12) are ejected simultaneously. The ejecting force needed for this requires a mechanically stable, compact construction which necessarily leads to an increased mass of the pipetting head. The greater mass results in greater inertia and accordingly conflicts with the desire for a horizontal movement with high acceleration.

An automatic pipettor with a vertically movable single-row, multi-channel pipetting head with a row of 12 pipette tips and a horizontally displaceable table is known from U.S. Pat. No. 4,478,094. The row of pipette tips is oriented orthogonal to the displacement direction of the table, so that a 96-well MTP is filled in 8 positioning steps which are carried out by stepwise horizontal displacement of the table. The tip ejector arrangement in this case comprises an ejector plate which is slotted in comb-like fashion and which can be lowered via two rods guided vertically in the housing of the pipettor. The ejector plate encloses the cone-shaped ends of the pipettes above the pipette tips, so that all of the pipette tips are stripped off simultaneously when the ejector plate is lowered. The required ejection force is generated in that the torque of a motor is transmitted via a pinion to a rack. The force generated in vertical direction when the tips are ejected presupposes a sturdy construction of the connection of the pipetting head with the base plate. Since only one horizontal relative movement between the row of pipettes and the MTP is possible, namely, in orthogonal direction to the row of pipettes, only MTPs having the same number of wells on a grid line oriented in the direction of the pipette row as the number of pipettes in a pipette row can be filled. The speed at which the entire MTP is filled and, therefore, the sample throughput are limited by the inertia of the table.

OBJECT AND SUMMARY OF THE INVENTION

It is the primary object of the invention to improve an automatic pipettor of the type described above in such a way that an appreciably higher sample throughput is made possible and the automatic pipettor can be used in an all-purpose manner for different MTPs. Also, the tip ejector mechanism is developed further in such a way that the required tip ejection force is reduced and it is accordingly possible for the mass of the moving pipetting head to be reduced appreciably.

This object is met according to the invention in that the pipetting head is movable in orthogonal direction to the row of pipettes, in that the ejector mechanism has a shaft oriented in the direction of the row of pipettes, a quantity of push-off units equal to the quantity of pipettes being fastened to this shaft so as to be offset at an angle relative to one another, each of which successively comes into contact with a strip-off unit guided in the direction of the pipettes during rotation of the shaft, displaces it, and strips a pipette tip from the pipette, and in that a lifter is arranged below the receptacle place and raises and lowers the microtitration plate in direction of the pipettes and can offset it in the direction of the row of pipettes.

An embodiment example which make use of the invention is described more fully in the following with reference to a drawing.

DESCRIPTION OF THE PREFERRED EMBODIMENTS

Figure 1:
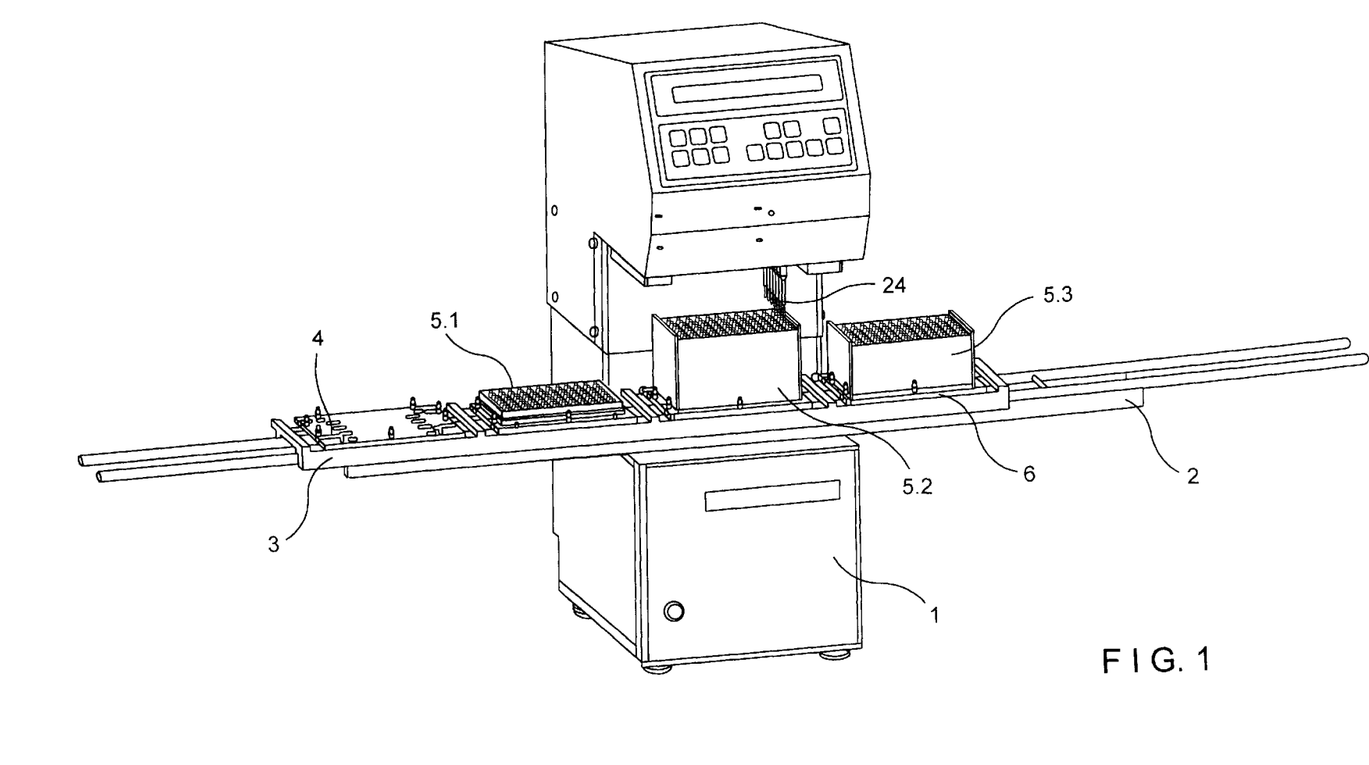
FIG. 1 shows an overall view of an automatic pipettor.

The view of the automatic pipettor in FIG. 1 essentially shows a base body 1 which can be set up on a horizontal plane, a first guide path 2 which is rigidly connected with the latter and on which a carriage 3 with four receptacle places 4 is guided linearly in horizontal direction below a row of pipette tips 24. Different vessels 5, for example, a 96-well MTP 5.1, a tip vessel 5.2 or a supply vessel 5.3 cap be received on the receptacle places 4. The outer dimensions of the vessels 5, also those of the MTPs, not shown here, with a greater number of wells, are substantially identical. Deviations can be compensated by an adapter plate 6.

Figure 2:
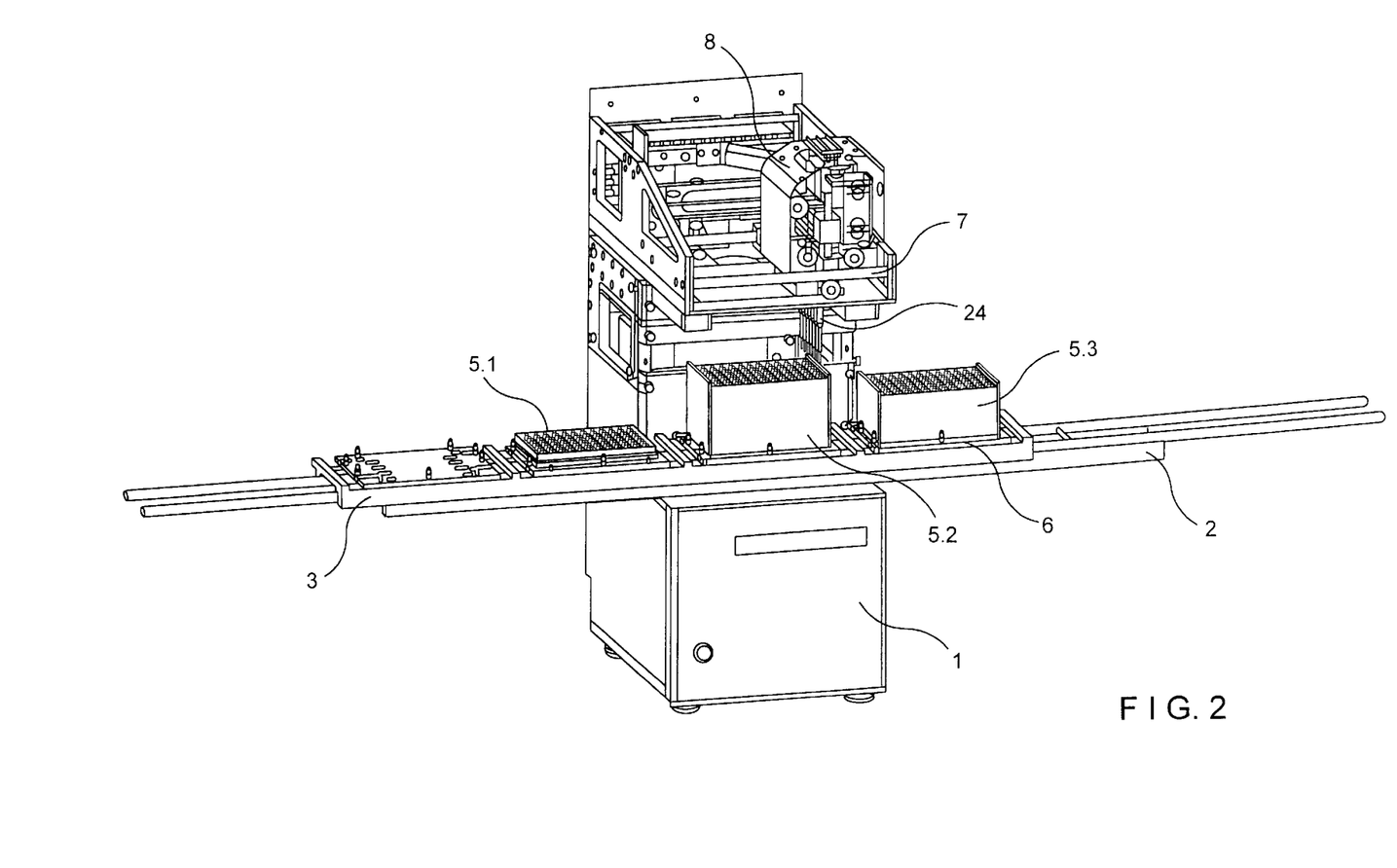
FIG. 2 shows the automatic pipettor shown in FIG. 1 with open housing.
Figure 3A:
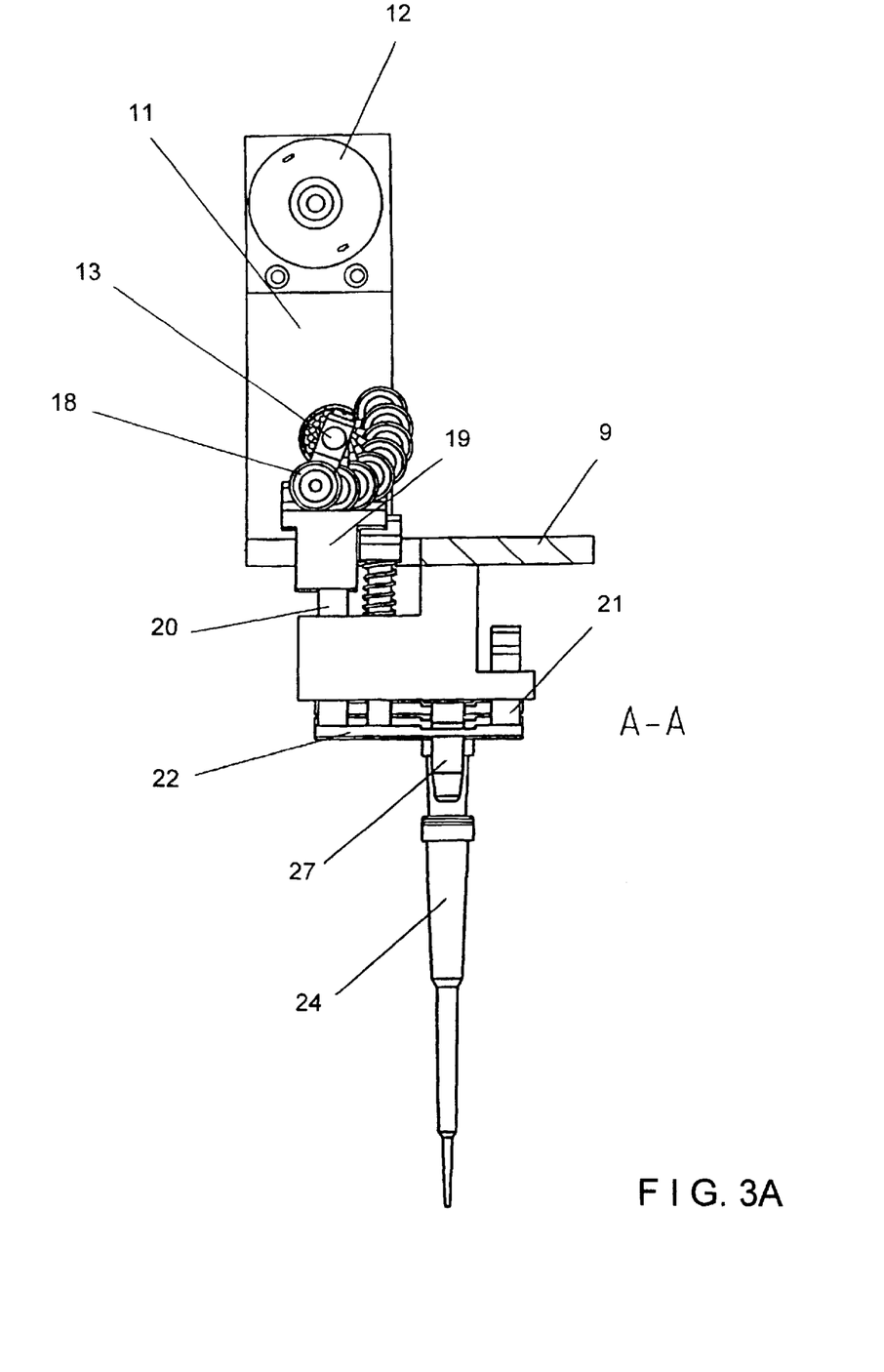
FIGS. 3A to 3E show different views of a tip ejector mechanism.
Figure 3B:
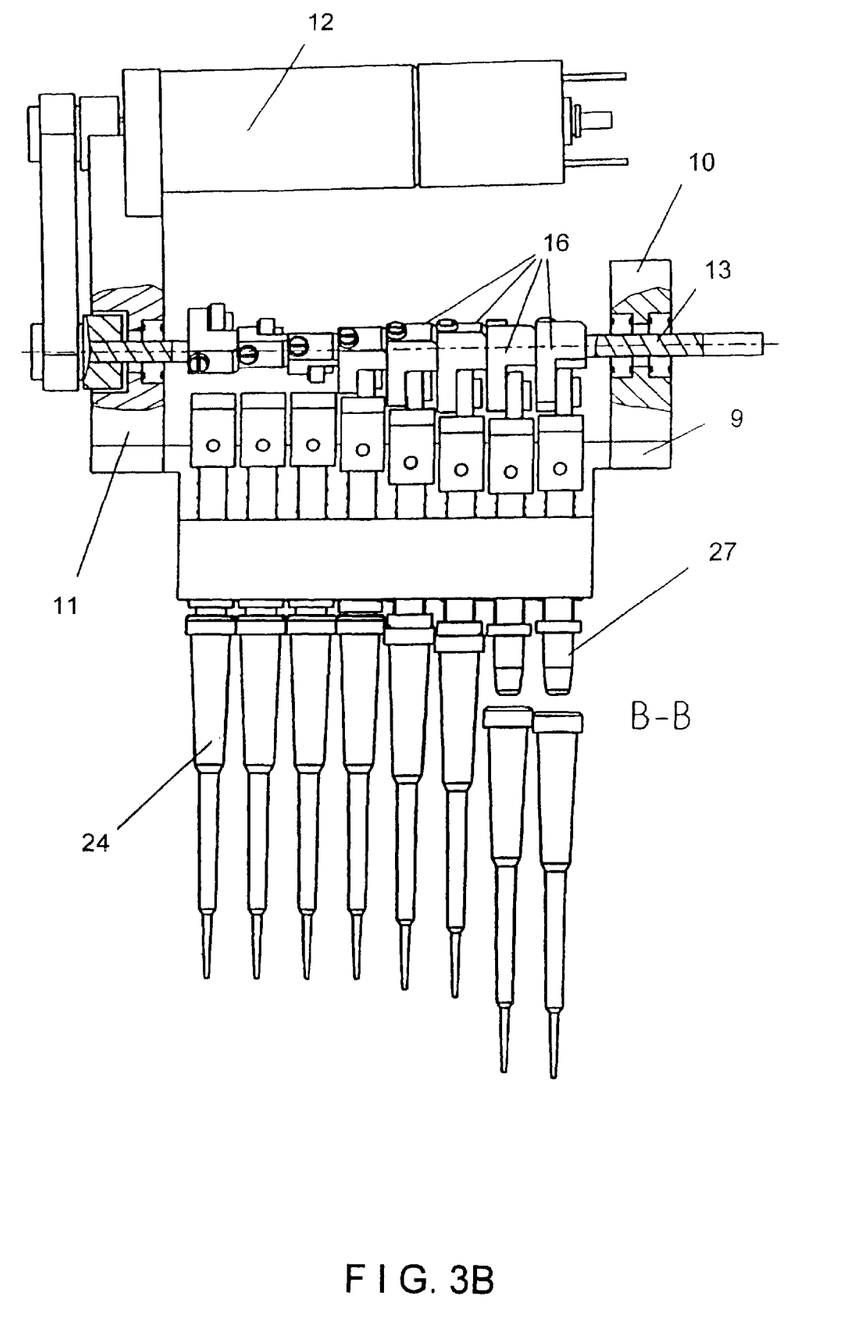
Figure 3C:
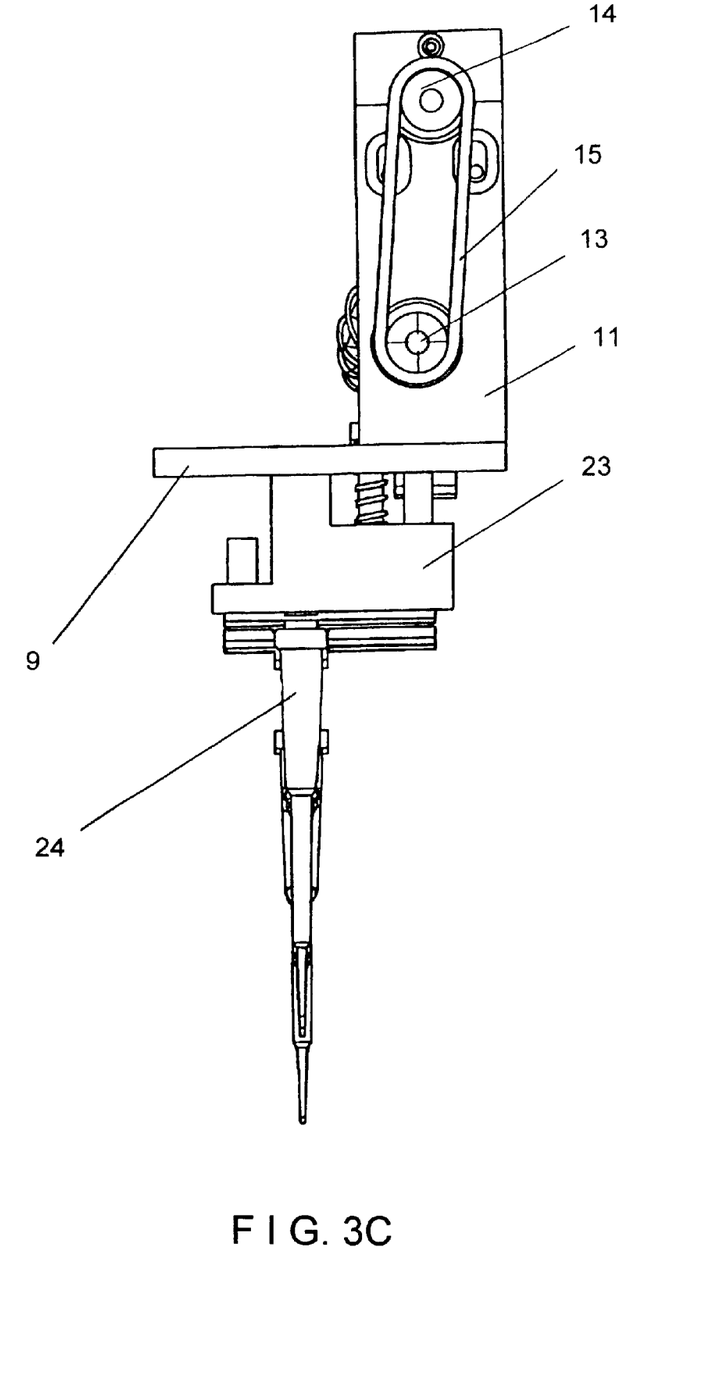
Figure 3D:
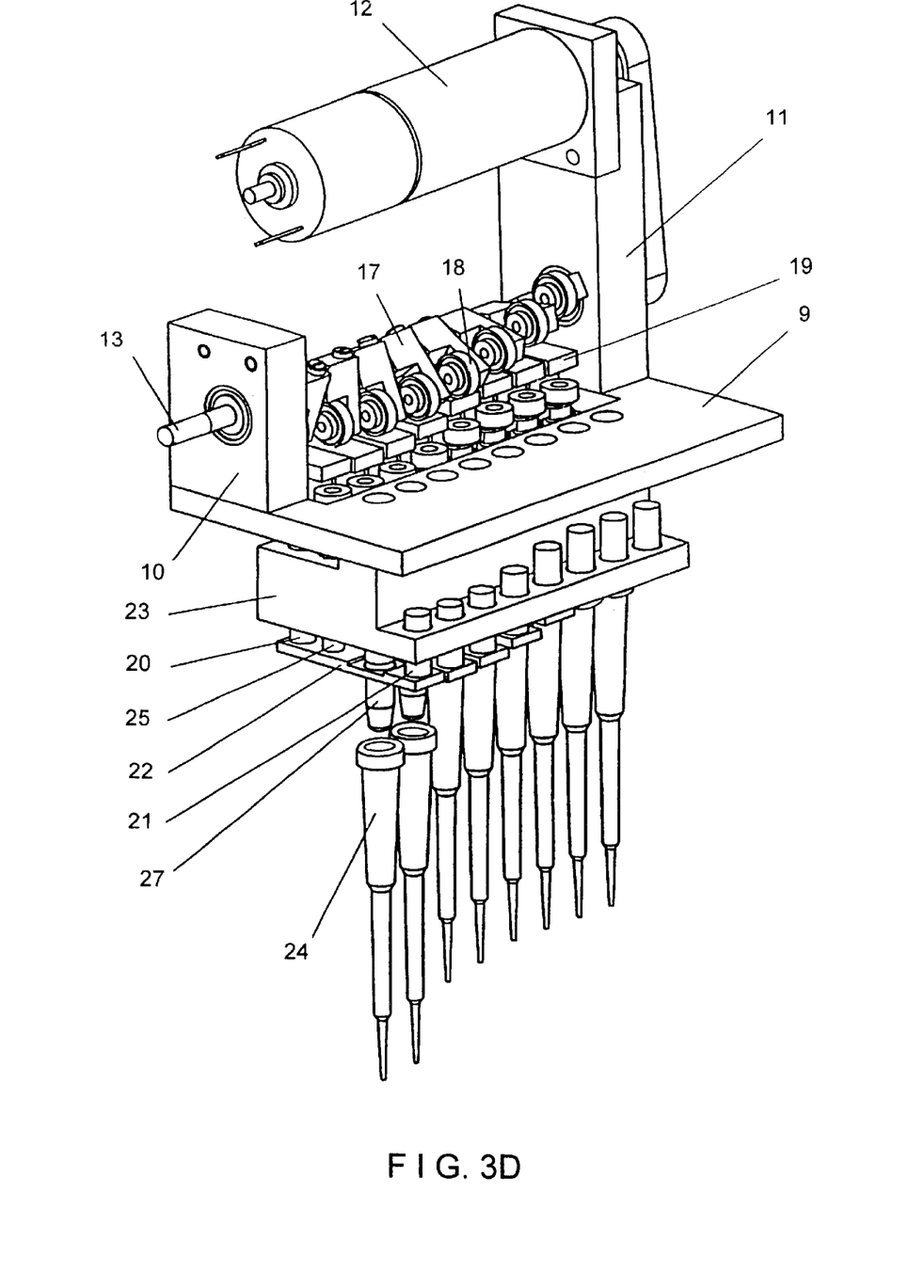
Figure 3E:
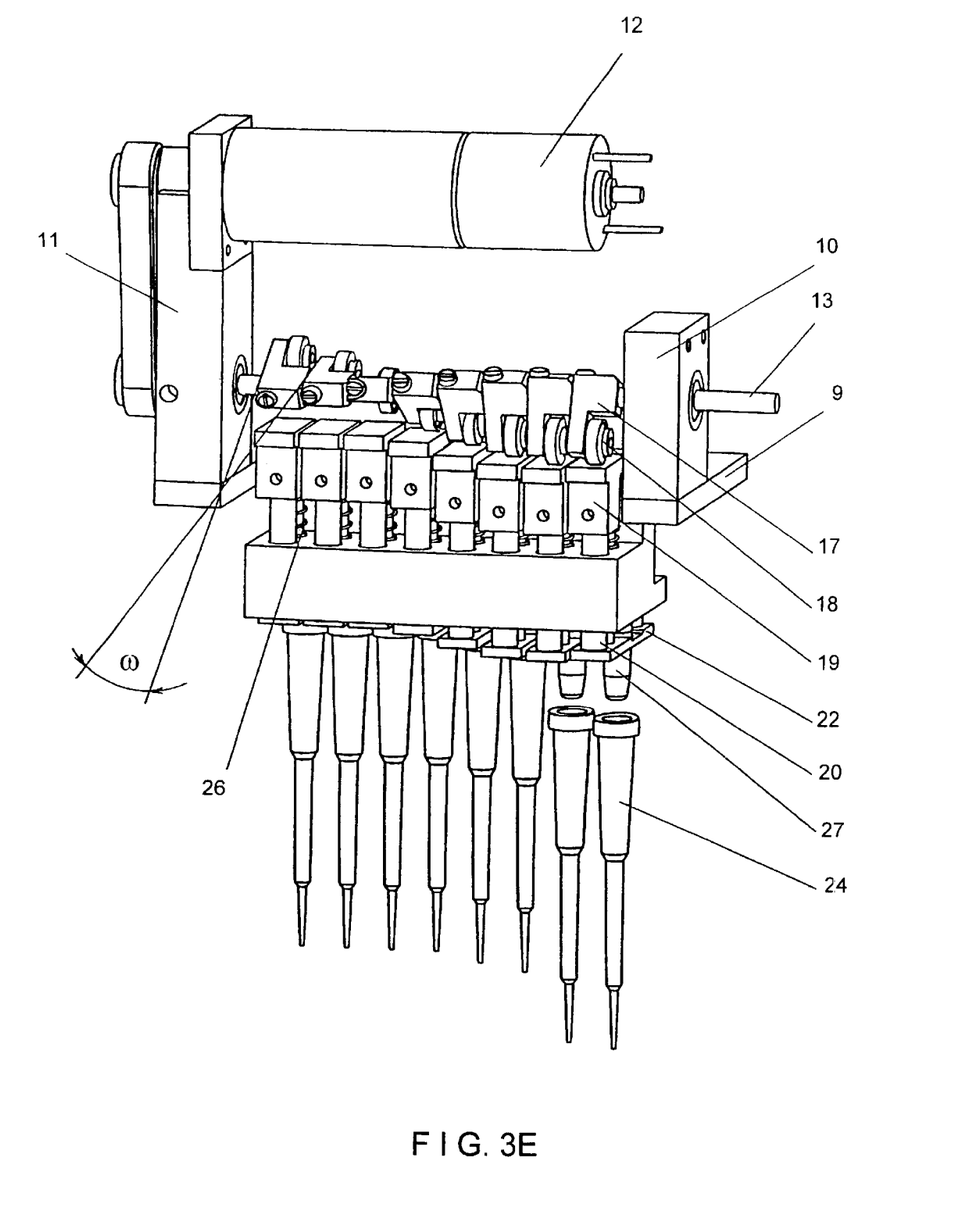

As can be seen in FIG. 2, a second guide path 7 is provided at the base body and is likewise rigidly connected therewith. A pipetting head 8 is movable on this second guide path 7 by means of a slide parallel to the carriage 3 along the length of a vessel 5 which is positioned below it. A lifter, not visible, is arranged below the moving area of the pipetting head 8 and serves to lift the vessel 5 located above it in the direction of the pipette tips 24.

The pipetting head 8 must be constructed so as to be as light as possible so that it can be moved with high acceleration. This is achieved by means of the construction of the tip ejector mechanism, which construction is essential to the invention and will be described more fully with reference to FIGS. 3A to 3E.

The base for the tip ejector mechanism is formed by a base plate 9 which is indirectly rigidly connected with the above-mentioned slide. A first and second side plate 10, 11 serving to fasten a motor 12 and to support a shaft 13 on both sides is arranged at this base plate 9. The torque of the motor is transmitted to the shaft 13 via a driven pinion 14 and a toothed belt 15.

In accordance with the quantity of pipette tips, eight, in this case, eight push-off units 16 are fixedly mounted on the shaft 13. The push-off units 16 form an arm 17 which is directed radial to the shaft 13, a ball bearing 18 being fastened to the free end of the arm 17 via its inner ring. The arms 17 are fastened to the shaft 13 so as to be offset relative to one another by an identical angle ω, so that they successively come into contact with a pressing piece 19 arranged below the shaft 13 when the shaft 13 rotates.

Figure 4:
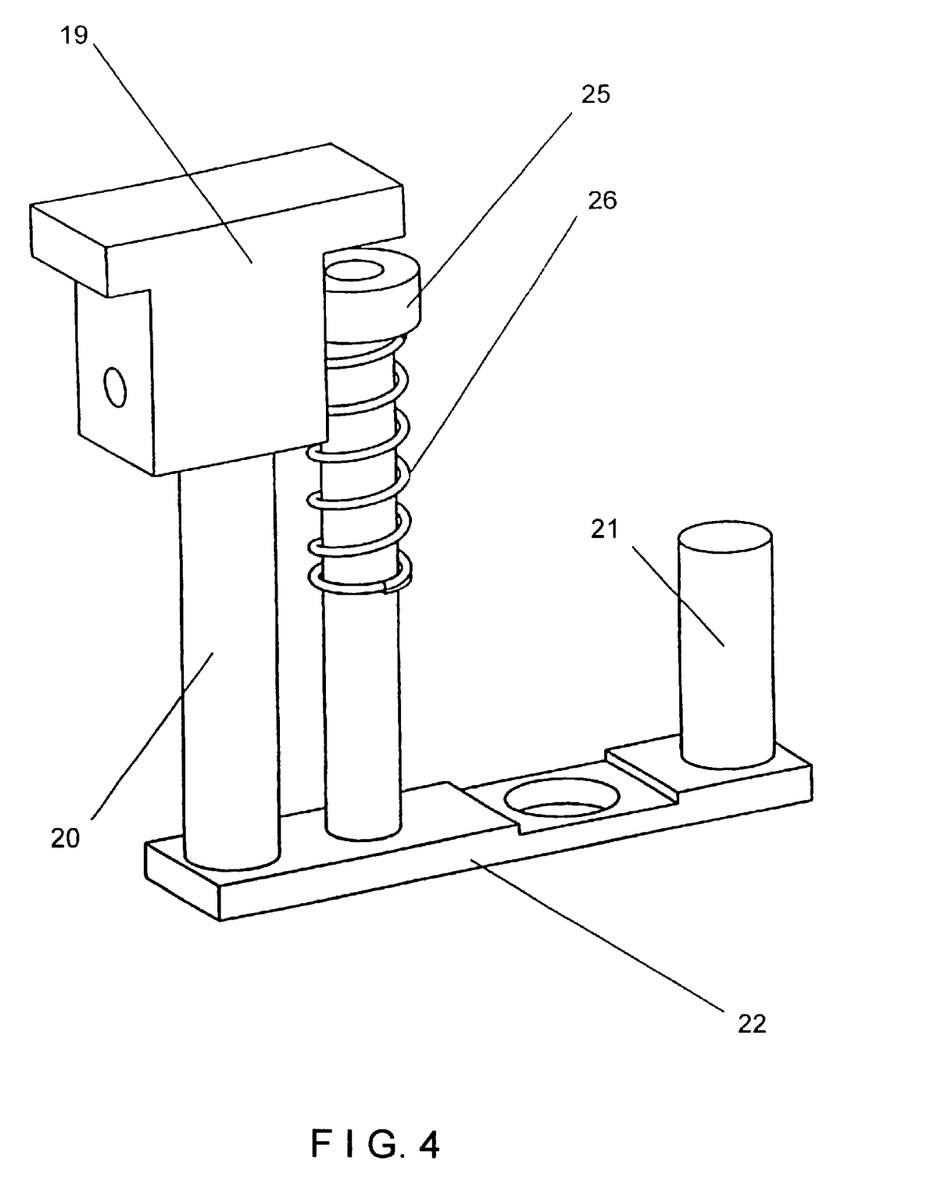
FIG. 4 shows a strip-off unit.

The pressing pieces 19 are a component part of a strip-off unit as is shown in FIG. 4. Each of the strip-off units is formed of a first and second guide rod 20, 21 whose first ends are connected with one another via a strip-off plate 22, the strip-off unit being guided vertically via the guide rods 20, 21 in a base body 23 which is fixedly connected with the base plate 9. A rod 25 with a pressure spring 26 is provided at the strip-off plate 22 parallel to the guide rods 20, 21, this pressure spring 26 contacting a collar formed at the rod 25 on one side and the base member 23 on the other side. Cutouts are located in the strip-off plates 22, the pipettes 27 held in the base member 23 projecting through these cutouts. The pipette tips 24 are attached to the free ends of the pipettes 27 which are conical.

The operation of the tip ejector mechanism will be described in the following. For better understanding of this operation, FIGS. 3D and 3E in particular show a work position of the tip ejector mechanism in which a portion of the pipette tips 24 has already been ejected from the pipettes 27, while other pipette tips 24 still sit on the conical ends of the pipettes 27.

Driven by the motor 12, the shaft 13 rotates, so that the ball bearings 18 come into contact successively with a pressing piece 19. The pressure pieces 19 are pressed downward vertically as the ball bearing 18 rolls against the spring force of the pressure springs 26 until the arm 17 is flush with the first guide rod 20, wherein the respective strip-off plate 22 strips off the pipette tip 24 from the associated pipette 27. While the shaft 13 continues to rotate, the ball bearing 18 subsequently moves out of the contact area with the pressing piece 19 which is simultaneously returned to its initial position by the pressure spring 26. The force required for stripping off the pipette tips 24 is needed only along a short movement area which is defined by the point in time at which the strip-off plate 22 comes into contact with an edge formed at the pipette tip 24 until the pipette tip 24 falls off. In order to eject all of the pipette tips 24 with the least possible force, the tip ejector mechanism is dimensioned in such a way that only one ejector unit is located in a position inside the described movement area.

Since the force required for ejecting all of the pipette tips 24 is equal to the force required for ejecting only one pipette tip 24, the pipetting head 8 can have a lightweight design regardless of the quantity of pipettes 27. The more lightweight the pipetting head 8, the higher the possible acceleration for carrying out the positioning steps, which allows a greater speed of the sample throughput.

In order to be able to use the automatic pipettor in an all-purpose manner for different MTPs, an additional horizontal relative movement in the direction of the row of pipettes is required. This is accomplished by the lifter.

While the foregoing description and drawings represent the present invention, it will be obvious to those skilled in the art that various changes may be made therein without departing from the true spirit and scope of the present invention

REFERENCE NUMBERS 1 base body
2 first guide path
3 carriage
4 receptacle place
5 vessel
5.1 96-well MTP
5.2 tip vessel
5.3 supply vessel
6 adapter plate
7 second guide path
8 pipetting head
9 base plate
10 first side plate
11 second side plate
12 motor
13 shaft
14 driven pinion
15 toothed belt
16 push-off unit
17 arm
18 ball bearing
19 pressing piece
20 first guide rod
21 second guide rod
22 strip-off plate
23 base member
24 pipette tip
25 rod
26 pressure spring
27 pipettes

What is claimed is:

1. An automatic pipettor with a single-row, multi-channel pipetting head, with a tip ejector mechanism for removing the pipette tips attached to the pipettes arranged in a row, and a receptacle place for microtitration plates below the pipetting head, comprising:

said pipetting head being movable in orthogonal direction to the row of pipettes;

said ejector mechanism having a shaft which is oriented in the direction of the row of pipettes and to which a quantity of push-off units equal to the quantity of pipettes are fastened so as to be offset relative to one another at an angle $\omega$, each of which successively coming into contact with a strip-off unit guided in the direction of the pipettes during rotation of the shaft, displaces it, and strips a pipette tip from a pipette; and a lifter being arranged below the receptacle place for raising and lowering the microtitration plate in direction of the pipettes.

2. The automatic pipettor according to claim 1, wherein the push-off units are arms which are oriented radial to the shaft and have a ball hearing fastened to the inner ring.

3. An automatic pipettor with a single-row, multi-channel pipetting head, with a tip ejector mechanism for removing the pipette tips attached to the pipettes arranged in a row, and a receptacle place for microtitration plates below the pipetting head, comprising:

said pipetting head being movable in orthogonal direction to the row of pipettes;

said ejector mechanism having a shaft which is oriented in the direction of the row of pipettes and to which a quantity of push-off units equal to the quantity of pipettes are fastened so as to be offset relative to one another at an angle $\omega$, each of which successively coming into contact with a strip-off unit guided in the direction of the pipettes during rotation of the shaft, displaces it, and strips a pipette tip from a pipette; and a lifter being arranged below the receptacle place for raising and lowering the microtitration plate in direction of the pipettes and being able to offset it in the direction of the row of pipettes.

4. The automatic pipettor according to claim 1, wherein the push-off units are arms which are oriented radial to the shaft and have a ball bearing fastened to the inner ring.

* * * * *